United States Patent
Reitz-Ausseur et al.

(10) Patent No.: US 11,702,626 B2
(45) Date of Patent: Jul. 18, 2023

(54) STRAINS OF PENICILLIUM CAMEMBERTI

(71) Applicant: Savencia SA, Viroflay (FR)

(72) Inventors: Joëlle Reitz-Ausseur, Les Essarts le Roi (FR); Richard Tallon, Orsay (FR); Amandine Dhaisne, Ablis (FR); Anne Goarin-Herve, Chevreuse (FR); Jérôme Soulie, Etriche (FR); Pierre Lacotte, Paris (FR)

(73) Assignee: Savencia SA, Viroflay (FR)

( * ) Notice: Subject to any disclaimer, the term of this patent is extended or adjusted under 35 U.S.C. 154(b) by 0 days.

(21) Appl. No.: 17/292,495

(22) PCT Filed: Nov. 12, 2019

(86) PCT No.: PCT/EP2019/081057
§ 371 (c)(1),
(2) Date: May 10, 2021

(87) PCT Pub. No.: WO2020/099427
PCT Pub. Date: May 22, 2020

(65) Prior Publication Data
US 2022/0017854 A1    Jan. 20, 2022

(30) Foreign Application Priority Data

Nov. 16, 2018 (FR) ...................... 1860633

(51) Int. Cl.
*C12N 1/14* (2006.01)
*A23C 19/032* (2006.01)
*C12R 1/80* (2006.01)

(52) U.S. Cl.
CPC ............ *C12N 1/145* (2021.05); *A23C 19/032* (2013.01); *C12R 2001/80* (2021.05)

(58) Field of Classification Search
CPC ........ C12N 1/145; C12N 1/14; A23C 19/032; A23C 19/061; A23C 19/0682; A23C 20/00; C12R 2001/80
See application file for complete search history.

(56) References Cited

FOREIGN PATENT DOCUMENTS

CN        103416489 A      12/2013

OTHER PUBLICATIONS

Lessard MH, Bélanger G, St-Gelais D, Labrie S. The composition of Camembert cheese-ripening cultures modulates both mycelial growth and appearance. Appl Environ Microbiol. Mar. 2012;78(6):1813-9. doi: 10.1128/AEM.06645-11. Epub Jan. 13, 2012. PMID: 22247164; PMCID: PMC3298135.*
Gillot et al., "1-Octanol, a self-inhibitor of spore germination in Penicillium camemberti," Food Microbiology, 57: 1-7 (2016).
Yousef et al., "Quantitation of Growth of Mold on Cheese," Journal of Food Protection, 50 (4): 337-341 (1987).
Abbas et al., "Penicillium camemberti," Encyclopedia of Dairy Sciences, Second Edition, 776-779 (2011).
International Search Report issued in corresponding International Patent Application No. PCT/EP2019/081057 dated Jan. 30, 2020.

* cited by examiner

*Primary Examiner* — Kade Ariani
(74) *Attorney, Agent, or Firm* — Morgan, Lewis & Bockius LLP

(57) ABSTRACT

The present invention relates to strains of *Penicillium camemberti* and to the use thereof for the preparation of food products, for example of dairy and/or vegetable origin, such as the ripening of soft cheeses having a moldy and/or mixed crust, in particular camembert.

6 Claims, 1 Drawing Sheet

STRAINS OF PENICILLIUM CAMEMBERTI

Figure 1:
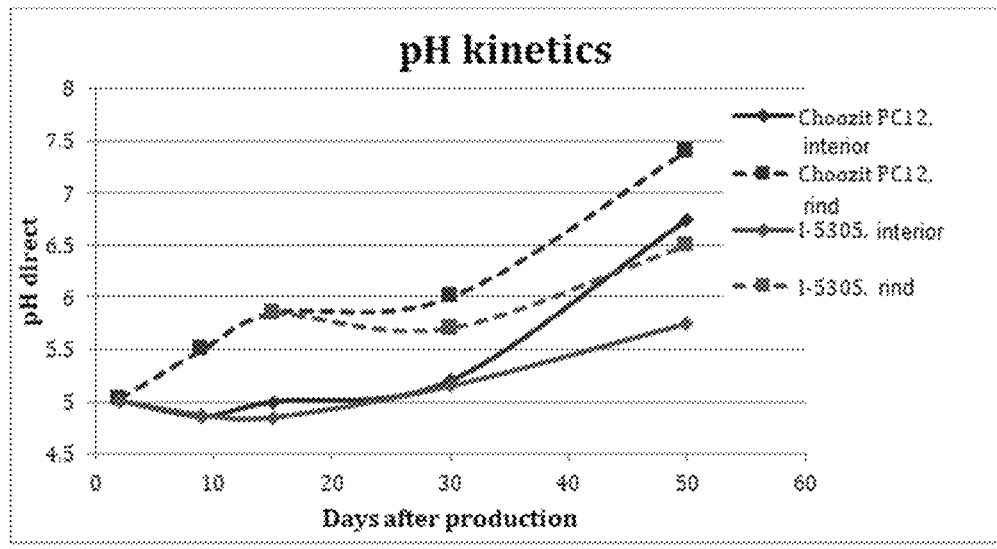

The present invention relates to novel strains of *Penicillium camemberti* and to the use thereof for the preparation of food products, for example of dairy and/or vegetable origin, such as the ripening of soft cheeses with a bloomy and/or mixed rind, in particular camembert.

The species *Penicillium camemberti* (*P. camemberti*) is an ascomycetic fungus used in cheese-making as surface flora on products, where it gives the latter their white "bloom" and where it contributes to the development of ripening through its lipolytic, proteolytic properties and its deacidifying ability. This fungus is also referred to as *Penicillium album*, *Penicillium candidum* or also *Penicillium biforme*.

Ripening is one of the production steps of a traditional cheese with a bloomy and/or mixed rind which follows other standard steps of:
curdling, in which the milk is left to coagulate through the action of a coagulant and lactic-acid producing ferments. The coagulant is traditionally rennet extracted from one of a calf's stomachs and consists of the enzymes chymosin and pepsin. Today, it is most often replaced by coagulants of microbial or vegetable origin, which are also known by a person skilled in the art as "rennet". The term is also used with this meaning in the following to describe any coagulant used in cheese production, regardless of its origin,
forming, shaping the curd obtained after the curdling step,
draining, consisting of separating the curd, the solid phase, from the whey, the liquid phase, and
salting, which determines the future taste of the cheese and which can be done either by soaking in brine or by dry sprinkling over the surfaces of the cheese.

After the salting step, the cheese is covered on all sides with *P. camemberti* to carry out the ripening step; alternatively or additionally, the ripening flora can also be mixed with the milk before the curdling step. During this ripening step, the cheese undergoes various transformations due to the double action of an enzyme and micro-organisms on the surface and inside the cheese. The salt migrates into the soft cheese and the rind begins to form. Then the ferments in the milk take over, which play an important part with regard to the flavour of the cheese. Lastly, the ferments on the surface in particular, i.e. bacteria, yeasts, fungi, in particular *P. camemberti*, complete this maturing process.

Known *P. camemberti* ferments include commercial ferments such as Danisco_Choozit PC 12 HYP 50 D V3®, Danisco Choozit PC NEIGE LYO 2 D®, Cargill_TC_PCTAM5_FR_210208®, SACCO_PCV5®, Danisco_Choozit-Ripening-Mould-Cultures®, O2_22_VS_ABL_HP6_SAM3® and neige CHR Hansen Brand—*Penicillium candidum* PCA1, PCA3, TT033®.

A bloomy rind is the rind which develops on the surface of the cheese from the growth of a surface flora of the *Penicillium* or *Geotrichum* type (such as *Geotrichum candidum*), it generally has a white and fluffy appearance; a mixed rind is a rind obtained by the growth of a surface flora combining at least one *Penicillium* type strain and at least *Geotrichum* type strain (such as *Geotrichum candidum*), or at least one *Penicillium* type strain or at least one *Geotrichum* type strain (such as *Geotrichum candidum*) and at least one other surface strain.

However, cheeses with a bloomy and/or mixed rind using these known ferments of *P. camemberti* may have problems with regard to rind quality and/or ageing that does not allow them to be stored long enough to be exported. Examples of rind quality problems include an undesirable rind colouring (e.g. yellowing, greying), a thick rind or also too strong a taste.

In this context, the inventors have identified novel strains of *P. camemberti* with a longer lag time, in particular longer than 19 days, useful in particular for correcting problems of rind quality and slowing down the biological ageing of cheeses with a bloomy and/or mixed rind.

The subject-matter of the present invention is thus a strain of *Penicillium camemberti* with a lag time on dairy culture medium at 4° C. of more than 19 days and preferably more than 20, 21 or 22 days.

In the context of the present invention, a lag time is defined as a time interval between sowing a strain on a culture medium and the visually perceptible appearance of the mycelium of said strain.

Dairy culture medium is defined as an agar culture medium comprising milk and/or caseins and/or milk fat and/or lactose . . . ; it can consist for example of milk agar media, tributyrin agar . . . ; preferably, the dairy culture medium is an MRP medium, the composition of which is detailed in the following experiment section.

The strain of *P. camemberti* of the present invention can be selected from a group including the strains: I-5311, I-5304, I-5307, I-5308, I-5305, I-5302, I-5309 and I-5310 and preferably from a group including the strains: I-5307, I-5308, I-5305, I-5302, I-5309 and I-5310.

The *P. camemberti* strains of the invention have been registered with the CNCM (Collection Nationale de Cultures de Microorganismes, National Collection of Microorganism Cultures) under the numbers:
I-5311, 5 Apr. 2018,
I-5304, 5 Apr. 2018,
I-5307, 5 Apr. 2018,
I-5308, 5 Apr. 2018,
I-5305, 5 Apr. 2018,
I-5302, 5 Apr. 2018,
I-5309, 5 Apr. 2018,
I-5310, 5 Apr. 2018.

Preferably, the *P. camemberti* strain of the present invention also has a recovery rate on milk culture medium at 4° C. of less than 0.15 cm/day, preferably less than or equal to 0.12 cm/day, 0.10 cm/day or also 0.05 cm/day.

The recovery rate of a strain is defined as the radial growth rate of the strain obtained by a simple linear model of the diameter of colonies as a function of time; the recovery rate being the directing coefficient of the regression line.

According to this preferred embodiment the strain of *P. camemberti* according to the invention is selected from a group including the strains: I-5311, I-5305 and I-5310 and preferably from a group including the strains: I-5305 and I-5310, more preferably the strain of *P. camemberti* according to the invention is strain I-5305.

According to another subject-matter, the present invention relates to the use of at least one of the strains of *P. camemberti* as defined above for the production of cheeses with a bloomy and/or mixed rind, or in the production of analogues of cheeses with a bloomy rind.

The cheeses, low-fat cheeses and cheese specialities having a bloomy and/or mixed rind according to the invention can be produced from cow's milk, goat's milk, sheep's milk, buffalo milk, camel milk, reindeer milk, yak milk, any species of mammal or a mixture of different milks; the cheeses with a bloomy and/or mixed rind are for example camemberts, bries, chaource, coulommiers, Brillat Savarin, Saint Albray, Le montagnard, goat's cheese log; in particular camembert.

Analogues of cheeses with a bloomy rind according to the invention are all products other than those defined in Decree no. 2007-628 of 27 Apr. 2007 relating to cheeses and cheese specialities; for which the production process includes a ripening step, leading to the development of a rind based on *P. camemberti*, with or without other strains.

Preferably, the strain of *P. camemberti* as defined above is used for producing cheeses with a bloomy and/or mixed rind based on cow's milk or goat's milk.

Due to their particular properties, the strains of *P. camemberti* according to the invention make it possible to improve the texture and/or the taste and/or the colour of the rinds; the rinds obtained can thus advantageously be less thick and/or less granular and/or less sandy and/or with a more neutral taste than the rinds produced with only commercial strains of *P. camemberti*, and this whether the cheese is low-fat or fat-enriched.

Furthermore, the cheese rinds with a bloomy and/or mixed rind produced with commercial strains of *P. camemberti* rapidly develop a coloration (grey, yellow in particular) after ripening; the strains of *P. camemberti* according to the invention can remedy this defect and can produce a whiter and/or less yellow rind, i.e. without colouration and/or with a less intense colouration.

More particularly, the cheese with a bloomy and/or mixed rind obtained with a strain of *P. camemberti* according to the invention has a surface with a smoother and more homogenous appearance and/or a cutting resistance with a rind integral to the soft cheese, in comparison with a cheese with similar physicochemical characteristics, and of the same age, made with commercial strains of *P. camemberti*.

The *P. camemberti* strains according to the invention may also allow the preparation of cheese with a bloomy and/or mixed rind which is less bitter and has a less pronounced earthy taste than those cheeses obtained with certain commercial strains of *P. camemberti*, in particular at the end of ageing.

Advantageously, the cheeses with a bloomy and/or mixed rind obtained with a strain of *P. camemberti* according to the invention retain excellent organoleptic qualities (in particular, texture, taste, smell) for a longer period than cheeses with a bloomy or mixed rind obtained by ripening with commercial strains (see experiment part); the usual consumption period for similar produces can thus be extended by several days. This advantage makes it possible in particular to transport these cheeses to places where they are consumed that are remote from their place of production.

The present invention therefore also relates to the use of a *P. camemberti* strain as defined above for ripening cheeses with a bloomy and/or mixed rind. By using this strain, the ripening of the cheese is sufficiently slow to allow applications which were not previously possible with a satisfactory quality and shelf life, or the use of non-dairy ingredients and/or additives (in the case of specialty cheeses). These applications include, but are not limited to, export.

The ripening of a cheese with a *P. camemberti* strain as defined above is performed in conditions known by a person skilled in the art allowing the growth of *P. camemberti*. For example, the ripening can be carried out in suitable containers which have walls with selective permeability and at a temperature suitable for the growth of the strain.

In one particular embodiment, the *P. camemberti* strain according to the invention can be associated with at least one other surface strain.

The inventors have shown that even when a *P. camemberti* strain according to the invention is combined with at least one other surface strain, the cheese with a bloomy and/or mixed rind refined with this mixture has an improved quality; this improvement can in particular concern the evolution of the colour of the rind, its texture (fine and not very perceptible in the mouth), as well as a weaker smell.

A surface strain is defined as a microorganism, added voluntarily by the person skilled in the art, which is useful for the formation of the rind; for example a mould, a bacterium or a yeast.

A surface strain means any type of microorganism which when developing on the surface of a cheese will participate in the formation of a rind and contribute to the ripening.

Preferably, *Geotrichum candidum, Penicillium fuscoglaucum, Penicillium biforme, Penicillium album, Fusarium domesticum, Debaryomyces hansenii, Kluveromyces lactis, Kluveromyces marxianus, Brevibacterium linens, Arthrobacter globiformis, Staphylococcus xylosus, Staphylococcus scuiri, Staphylococcus succinus, Micrococcus caseolyticus, Micrococcus conglomeratus, Corynebacterium casei, Hafnia alvei* are chosen as surface strains.

More preferably, the *P. camemberti* strain according to the invention is used in combination with at least *Geotrichum candidum* in a ratio of *P. camemberti* to *Geotrichum candidum* greater than 0.5, ranging from 0.5 to 0.99 and preferably from 0.8 to 0.99.

In one embodiment of the invention, the *P. camemberti* strain is used in combination with at least one commercial strain of *Penicillium camemberti*, for example in a ratio which can range from 0.2 to 0.80.

In another embodiment of the invention, the *P. camemberti* strain according to the invention is used alone.

The inventors have also found that the *P. camemberti* strains according to the invention allow the preparation of food products other than cheese and cheese analogues.

Thus, the present invention also relates to the use of at least one *P. camemberti* strain as defined above for fermenting a vegetable matrix; in this embodiment, the fermentation leads to the development of a rind which covers the vegetable matrix.

A vegetable matrix is defined in the present invention as any mixture of raw materials not derived from the Animal kingdom, which includes more particularly fruits and/or nuts and/or legumes and/or grasses and/or algae and/or fungi, and/or any products extracted or processed from these materials such as juices, flours, protein powders and starch powders, but not limited to the latter.

The vegetable matrix is such that it has a percentage of moisture which is sufficient to allow fermentation by the *P. camemberti* strain, and an activity of water (Aw) greater than or equal to 0.8, preferably greater than or equal to 0.9.

More generally, the invention is also directed to the use of at least one *P. camemberti* strain as defined above for fermenting a food product consisting of a mixture of a vegetable matrix and a dairy material, without there being any limitation with respect to the ratio of vegetable matrix to dairy material; in a particular embodiment of the invention, said mixture comprises at least 30% vegetable matrix.

Dairy material means milk, any product derived from milk such as skimmed or unskimmed milk powder, milk proteins, milk fat which can be derived from milk cream, butter, standardised anhydrous milk fat and/or a material derived from fractionating an anhydrous fat material, carbohydrates (lactose for example), minerals or a mixture thereof as well as any product made from milk, for example by coagulation of milk, such as cream, butter, yoghurt, cheese; for example rennet casein, firm or semi-firm low-fat or partly low-fat cheeses, low-fat or partly low-fat soft cheeses, sodium, potassium or calcium caseinates.

The present invention also relates to a method for the preparation of a food product comprising a step of fermentation with at least one *P. camemberti* strain as defined above, said food product can be a cheese, a vegetable matrix or a mixture of a vegetable matrix and a dairy material.

More specifically, when the method according to the invention relates to the preparation of cheese, it can comprise the following steps, in any order:
a) optionally, an ultrafiltration step of the milk;
b) addition of microorganisms of dairy interest and rennet to the milk or retentate;
c) dosing of the retentate if the method comprises a step of prior ultrafiltration;
d) curdling of the milk or retentate;
e) forming the curd;
f) draining the curd consisting of separating the curds and whey, if the method does not include a step of prior ultrafiltration;
g) salting the curd by soaking in brine or by sprinkling salt on the surfaces of said curd or in the mass;
h) ripening the cheese obtained in step g);
said method is such that this *P. camemberti* strain is applied to the surface of the cheese just before the ripening step h) and/or mixed directly with the milk or retentate together with the microorganisms of dairy interest and the rennet during step b).

This method applies to any cheese, regardless of the its fat content and in particular to a low-fat or fat-enriched cheese.

More particularly,
the optional ultrafiltration step can be performed between 4 and 60° C. and produces a retentate containing between 85 and 200 g/kg proteins and a ratio of fats/proteins of between 0 and 1.5; said retentate can then be mixed with cream to raise the latter ratio to 3.2;
the microorganisms of dairy interest and rennet are added to the milk or to the retentate (in case of ultrafiltration) or to the standardised mixture (in case of fat-enhanced products by adding cream or in the case of low-fat products);
the curdling can be performed on the milk or the retentate or also the standardised mixture;
the forming can be carried out by extrusion.

The strains of microorganisms of dairy interest used in the method of the invention are those generally used for manufacturing cheese with a bloomy and/or mixed rind and are known by the person skilled in the art; it may for example consist of mesophilic lactic ferments (*Lactococcus lactis* ssp *lactis* and/or *Lactococcus lactis cremoris, Lactococcus lactis* ssp *lactis biovar diactylactis, Leuconostoc lactis* and/or *Leuconostoc mesenteroides*) or thermophiles (*Streptococcus thermophilus, Lactobacillus delbrueckii* subsp. *bulgaricus* and/or *Lactobacillus casei* and/or *Lactobacillus brevis*).

The method according to the invention, in the case of a vegetable matrix or a mixture of a vegetable matrix and a dairy material, may comprise the following steps, in any order:
a) mixing the raw materials forming the vegetable matrix, such as those defined above;
b) optionally adding dairy material;
c) pasteurising the vegetable matrix or said mixture;
d) forming the product obtained in step c);
e) inoculating with at least one strain of *P. camemberti* according to the invention; the inoculation can be performed by immersion and/or spraying;
f) fermenting said product obtained in step e).

More particularly,
the mixture of raw materials forming the vegetable matrix can be performed at a temperature between 10 and 90° C., and a shear rate between 1 and 500 s$^{-1}$, preferably, the vegetable matrix is composed of a majority of seeds or nuts, the mixture is then prepared preferably at a temperature in the order of 20° C. and a shear rate in the order of 10 s$^{-1}$;
the pasteurisation of said vegetable matrix or said mixture is for example carried out at a temperature between 70° C. and 90° C., for a time between 60 s to 1800 s; preferably at a temperature of about 72° C. for about 900 s;
the forming can be carried out at a temperature between 10 and 25° C., preferably at 20° C.;
the fermentation can be carried out at a temperature below 30° C. until a homogenous rind develops.

According to a particular embodiment of the methods according to the invention as defined above, the fermentation step is carried out with a mixture of surface strains comprising at least one strain of *P. camemberti* according to the invention combined with at least one other surface strain as defined above.

Preferably, the mixture comprises a strain of *P. camemberti* according to the invention and at least *Geotrichum candidum*.

The present invention relates lastly to a food product obtained by one of the methods of the invention as defined above.

In particular, the present invention relates to a cheese with a bloomy and/or mixed rind obtained by the method of the invention; such a cheese is characterised by a time interval during which its organoleptic properties are optimal, longer than those of cheeses with a bloomy and/or mixed rind obtained by commercial *P. camemberti* ferments.

The present invention also relates to a food product composed of a vegetable matrix fermented with at least one strain of *P. camemberti* as defined above.

The present invention also relates to a food product composed of a mixture of a vegetable matrix and a dairy material fermented with at least one strain of *P. camemberti* as defined above; in particular, the mixture can be such that it comprises at least 30% vegetable material.

FIGURES

FIG. 1 pH kinetics in the interior and rind of cheeses, made with strain I-5305 and PC 12 (strain CHOOZIT PC12, Danisco).

Figure 2:
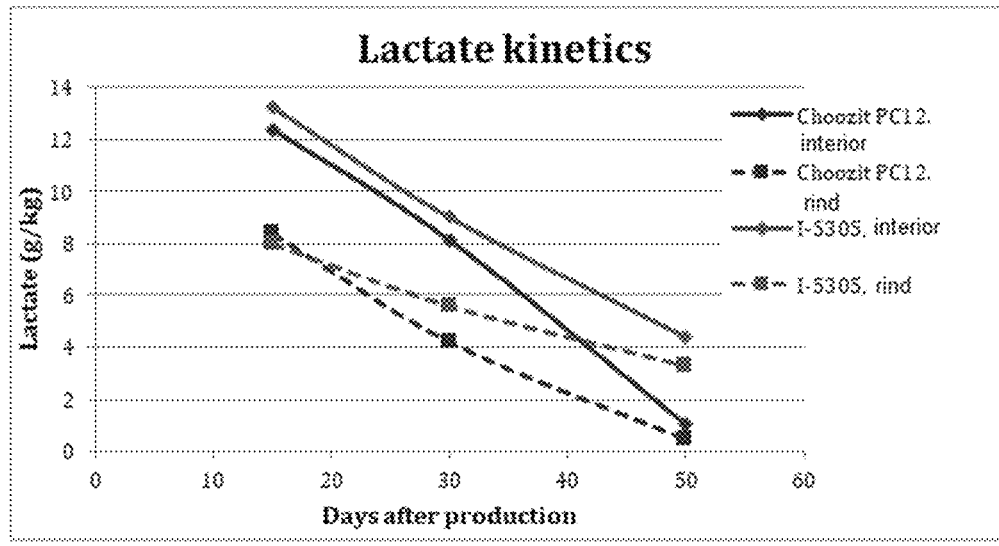

FIG. 2 Kinetics of the residual concentration of lactate in the interior and rind of cheeses, made with strain I-5305 and PC 12 (strain CHOOZIT PC12, Danisco).

EXAMPLE 1—CHARACTERISATION OF THE FUNCTIONAL PROPERTIES OF *P. CAMEMBERTI* STRAINS OF THE INVENTION

Materials and Methods:
a) Strains studied:
The strains studied are the following:
I-5302, I-5304, I-5305, I-5307, I-5308, I-5309, I-5310, I-5311 are kept frozen at −80° C., in the form of spores suspended in a 15% glycerol cryoprotectant. The spores are obtained after culture on a synthetic medium, solid medium of the PDA type (Potato Dextrose Agar marketed by Biokar), PC 12 and PC SAM3 (supplier: Danisco) are marketed in liquid form. They are kept frozen (at −80° C.) in a mixture consisting of 50% liquid ferment and 50% cryoprotectant at 30% glycerol, PCTN, PC PR1, PC TAM5 (supplier: Lallemand) and PC A1 swing (supplier: CHR HANSEN) are marketed in lyophilised form. They are kept frozen at −80° C., according to the following mixture 2 g lyophilisate+18 g cryoprotectant at 15% glycerol, b) Medium used:

The medium used is a dairy medium, the dairy and acidified MRP.

Media: Dairy model (MRP)

TABLE 1

Composition of MRP medium

|  | for 1 liter g |
|---|---|
| Milk base | 727 |
| Type E bacteriological agar | 18.2 |
| 90% pure lactic acid L | 9.1 |
| 50% sodium lactate | 9 |
| Casein acid hydrolysate | 0.09 |
| Sodium chloride | 11.8 |

The milk base is composed of 11.22% standard anhydrous milk fat, 11.48% ultra-filtered skimmed milk powder and 77.30% water.

c) Inoculation of the containers:

The dilutions are adjusted according to the cell count of the different ferments, in order to obtain isolated colonies and thus measure their diameter more easily.

d) Observations:

The containers are observed every day from D+3.

e) Observed parameters:

The growth of the strains is studied by measuring the radial growth (which enables the calculation of the recovery rate) and their lag time.

Measuring the recovery rate:

This is obtained by the daily measurement of the diameter of the colonies.

The recovery rate in cm per day is defined by the slope of the straight line obtained from the graph: diameter of colonies (cm) as a function of time (days).

Measure of the lag time:

Its calculation is made with respect to the equation of the line representing radial growth.

The strains tested have different physiological states which can be in liquid form, in the form of lyophilsate or which have been grown on agar medium.

Two series of characterisation were therefore launched one week apart, while respecting the day of inoculation to have identical reading days for both series.

Results:

The lag time:

TABLE 2

Measure of lag time on MRP medium at 4° C.

| Strain | Lag time (days) |
|---|---|
| PC PR1 | 16.26 |
| PC 12 | 16.59 |
| PC TAM5 | 16.91 |

TABLE 2-continued

Measure of lag time on MRP medium at 4° C.

| Strain | Lag time (days) |
|---|---|
| PC TN | 17.82 |
| PC A1 swing | 18.33 |
| PC SAM3 | 18.58 |
| I-5311 | 19.53 |
| I-5304 | 19.55 |
| I-5307 | 20.04 |
| I-5308 | 21.14 |
| I-5305 | 21.23 |
| I-5302 | 21.28 |
| I-5309 | 22.23 |
| I-5310 | 36.25 |

The recovery rate:

TABLE 3

Measure of recovery rate on MRP medium at 4° C.

| Strain | Recovery rate (cm/day) |
|---|---|
| I-5305 | 0.04 |
| I-5311 | 0.12 |
| I-5310 | 0.14 |
| PC TN | 0.16 |
| PC PR1 | 0.16 |
| PC TAM5 | 0.16 |
| PC 12 | 0.16 |
| I-5307 | 0.17 |
| PC SAM3 | 0.17 |
| PC A1 swing | 0.17 |
| I-5304 | 0.19 |
| I-5309 | 0.19 |
| I-5308 | 0.22 |
| I-5302 | 0.23 |

Results:

The commercial strains have a recovery rate of between 0.16 and 0.23 cm/day and a lag time of between 16 and 18 days.

The strains according to the invention (I-5311, I-5304, I-5307, I-5308, I-5305, I-5302, I-5309 and I-5310) have a longer lag time, systematically longer than 19 days on MRP medium at 4° C.

Furthermore, some of them (I-5305, I-5310 and I-5311) have a recovery rate of less than 0.15 cm/day, on MRP medium at 4° C.

The properties of the *P. camemberti* strains according to the invention make them excellent candidates for use for the slow ripening of cheeses with a bloomy and/or mixed rind, thus allowing the longer preservation of these cheeses.

EXAMPLE 2—USE OF DIFFERENT STRAINS OF *P. CAMEMBERTI* FOR THE PRODUCTION OF SOFT CHEESE WITH A BLOOMY RIND FROM A LACTIC CURD ENRICHED WITH FAT IN A VAT

Materials and Methods:

a) Description of the steps of production:

The method for preparing a soft cheese with a bloomy rind from a lactic curd enriched with fat in a vat comprises the following main steps:

cow's milk enriched by the addition of whole cream or retentate having the characteristics of a target of 30±5 g/l protein matter (PM) and 110±10 g/l fat (F), is pasteurised according to the standard procedures of a person skilled in the art, commercial mesophilic lactic ferments (2 and 10 g/l, such as for example a mixture of *Lactococcus lactis* ssp *cremoris, Lactococcus lactis* ssp *lactis, Lactoccoccus lactis* ssp *lactis biovar diacetylactis, Leuconostoc*) and ripening (comprising yeasts and moulds) are then added in the usual doses to make a lactic curd, the milk is renneted at a pH equal to or less than 6.50 in vats of 200 l-500 l in suitable doses and the milk is left to curdle, the forming is performed at a pH less than or equal to 4.90, the product is then left to rest before being removed from the moulds by turning over if necessary, the salting is carried out dry, the ripening step is performed before proceeding to packaging.

The *P. camemberti* strains can be inoculated either directly with lactic ferments and other ferments at doses between 0.1 to 2 doses per 100 l of milk (1 dose=$2.10^9$ spores/ml) or as a spray after salting at a dose between 0.4 and 5 doses/l of water.

b) Studied strains:

Strain I-5305 as well as strains VELV-TOP®PC 1131 of Lallemand and VELV-TOP®PC PR1 of Lallemand were each used for producing a cheese at the same doses and in the same conditions.

Organoleptic Results:

The soft cheeses with a bloomy rind produced with each of these strains were submitted to a panel of experts for an evaluation of the products after packaging at an optimum age (25-30 days) with regard to 4 criteria: external appearance, ease of cutting, texture and taste.

Table 4 below summarises the main advantages observed between the product made from strain I-5305 compared to products obtained with strain IB1 and with strain PR1. These comments are from two independent replicates.

TABLE 4

The main advantages observed between the product made with ferment I-5305 relative to the product made with ferment IB1 and ferment PR1.

|  | Advantages I-5305 versus IB1 | Advantages I-5305 versus PR1 |
| --- | --- | --- |
| External appearance | Even surface, no hollows | Ridges of product less marked |
| Ease of cutting and appearance when cut | Rind slightly less thick, less crisp | The rind is integral to the interior |
|  | The rind is integral to the interior | The interior is less fluid |
| Texture | Good when cut, less soft | Rind less perceptible in mouth |
| Taste | Less mature, less earthy, less bitter, more creamy, slight fungus | Less buttery |

*The date of inoculation is considered to be D + 1.

The cheese obtained with strain I-5305 makes it possible to obtain a product after packaging which is significantly whiter with a smoother and more homogenous surface; it has good cutting behaviour with a rind integral to the soft cheese, with a marked creamy taste with a typical fungus note with no defects at optimum tasting age, such as bitterness and earthiness.

The cheese obtained with strain I-5305 is judged, at the same age, to have a longer shelf life according to the established criteria of colour, lack of bitterness and smoothness below the rind which are desirable in a mature product.

EXAMPLE 3—USE OF DIFFERENT STRAINS OF *P. CAMEMBERTI* FOR PRODUCING A GOAT'S CHEESE IN VAT TECHNOLOGY

Materials and Methods:

a) Description of production steps:

The method of preparing a goat's cheese with vat technology with a 100% *P. camemberti* rind comprises the following main steps:

a goat's cheese enriched by the addition of cream then delactosed to 17% having the characteristics or a target of 33±2 g/l protein matter and 46±2 g/l fat, is pasteurised according to the standard methods used by a person skilled in the art, commercial mesophilic lactic ferments (for example a mixture of *Lactococcus lactis* ssp *cremoris, Lactococcus lactis* ssp *lactis, Lactoccoccus lactis* ssp *lactis* biovar diacetylactis, *Leuconostoc* at 3 g for 100 L) can be inoculated to enable cold maturation, from 0.15 to 0.2 pH unit, the material is then heat treated and preserved.

thermophilic lactic cultures are added (*Streptococcus thermophilus* at 4 g/100 l), the renneting of the milk is carried out at a pH equal to or lower than 6.35 in 200 l-500 l vats in suitable doses and left under serum, the forming is carried out at a pH lower than or equal to 6.40, the product is then left to rest before being demoulded by turning over as necessary at a pH of 5, the salting is carried out dry, the ripening step is performed before proceeding to packaging.

The *P. camemberti* strains can be inoculated either directly with the lactic ferments and other ferments at doses between 0.4 dose for 100 l milk or by spraying for 24 h after salting at 1 dose/l of water.

b) Studied strains:

Strain I-5305 as well as strains PC TN (VELV-TOP PC TN, Lallemand) and PC 12 (Danisco) are tested at the same doses and in the same conditions.

Organoleptic Results:

The soft cheeses with bloomy rind produced were submitted to a panel of experts for evaluation within the optical age window of D+28.

Table 5 below shows the main characteristics of cheeses inoculated with 50% PC 12 and PC TN and those having 100% of strain I-5305.

TABLE 5

Main characteristics of cheeses inoculated with 50% PC 12 and 50% PC TN and one having 100% CNCM I-5305 tasted by a panel of experts on D + 28.

| Composition of the inoculation of the rind | 50% PC 12 and 50% PC TN | 100% I-5305 |
|---|---|---|
| Appearance | White fluffy fairly extensive | Fluffy white but to a lesser extent, less relief, more level |
| Smell | Weak smell - fungus | Weak smell - more cave |
| Texture | Very medium - rind not very marked | Texture + melt - a little firmer - rind not very marked |
| Taste | Fungus taste very present Slight bitterness to finish | Fungus taste present- no bitterness |

Desirable characteristics of products marked in bold.

From a semi-ripened stage, there is clearly a qualitative advantage of the series of cheeses produced with I-5305 in all of the criteria required during the production of quality cheese with a bloomy rind.

EXAMPLE 4—USE OF DIFFERENT *P. CAMEMBERTI* STRAINS FOR PRODUCING LOW-FAT SOFT CHEESE WITH A BLOOMY RIND ACCORDING TO A METHOD OF ULTRAFILTRATION

Materials and Methods:
a) Description of production steps:
The method of preparation of a low-fat soft cheese with a bloomy rind according to a method of ultrafiltration comprises the following main steps:
  preparation of the precheese which comprises the retentate, the homogenised cream, the salt in the mass, the gelatine, the betacarotene,
  dosage and incorporation of mesophilic lactic ferments, *P. camemberti* and rennet,
  acidification at a pH lower than or equal to 5.35,
  cooling, demoulding and brining,
  drying,
  ripening,
  drying before packaging,
  packaging,
  storage.
b) Studied strains:
Strain I-5305 as well as strain PC 12 (strain CHOOZIT PC 12, Danisco) are tested at the same doses and in the same conditions.
Results:
a) Analytic results:
The pH kinetics carried out in comparison on the two cheeses reveals that the cheese made solely with strain PC 12 (CHOOZIT PC 12, Danisco) has a greater rise in pH both in the interior and in the rind by a delta of one pH unit at 50 days (FIG. 1).

From 30 days after production, the kinetics of residual lactate concentration within the two cheeses begin to diverge with a higher residual concentration on the rind and in the interior for the cheese made with strain I-5305. 50 days after manufacture, an evolution towards a stabilised core-rind equilibrium around a lactate concentration of 4 g/kg is observed for strain I-5305 in comparison with a much lower residual concentration for the cheese with strain PC 12 (CHOOZIT PC12, Danisco). The residual presence of lactate in the rind, on the optimum use-by date, makes it possible for the *Penicillium camemberti* strain to continue to consume lactate instead of proteins, which gives it a better taste on the optimum use-by date.

These results show significantly a cheese with a lower pH with rind when combined with strain I-5305. This more acidic pH limits the formation of an insoluble calcium layer that causes the formation of a granular rind, which is an organoleptic defect in soft cheese with a light bloomy rind obtained by an ultrafiltration process.

b) Organoleptic results:
The soft cheeses with a bloomy rind were submitted to a panel of experts for evaluation of the products at different stages of their life, to assess the evolutionary aspect of the product with regard to different criteria: external appearance, rind quality and taste.

Table 6 below summarises the main differences observed between the product made with strain CNCM I-5305 compared to the product made with strain PC 12 (CHOOZIT PC12, Danisco).

TABLE 6

Main differences observed between the product made from ferment I-5305 compared to the product made with ferment PC12

| | Young product (D − 21)* | Semi-mature product (D + 29) | Mature product at optimal use-by date (D + 50) |
|---|---|---|---|
| External appearance | | | Product much whiter |
| Quality of the rind | The cheese obtained with I-5305 has a softer rind, more runny, slightly grainy, less detached | The cheese obtained with I-5305 has a less grainy rind | The cheese obtained with I-5305 has a less detached, thicker, drier rind |
| Taste | The cheese obtained with I-5305 is more acidic, less ripened | | The cheese obtained with I-5305 has a less pronounced mould taste |

*The inoculation date is considered as D + 1.

These results show that, at an equivalent age, the benefits of cheese made with strain I-5305 may represent an improvement in quality during the period of the optimal use-by date.

EXAMPLE 5—USE OF A MIXTURE OF DIFFERENT *P. CAMEMBERTI* STRAINS FOR PRODUCING SOFT CHEESE WITH A BLOOMY RIND ACCORDING TO AN ULTRAFILTRATION METHOD

Materials and Methods:

a) Description of production steps:

The method for preparing low-fat soft cheese with a bloomy rind according to an ultrafiltration method in combination with other *P. camemberti* strains comprises the following main steps:
- preparing the precheese which comprises the retentate, the fermented milk, the cream,
- mixing with the preparation comprising added dairy proteins and flavouring,
- homogenising with degassing then heat treatment,
- incorporating lactic ferments (*Lactococcus lactis* ssp *lactis biovar diacetylactis, Streptoccocus thermophilus, Lactobacillus delbrueckii* ssp *bulgaricus*), of *P. camemberti* and rennet,
- dosing and acidification at a pH higher than or equal to 4.85,
- cooling, demoulding and brining,
- drying,
- ripening,
- drying,
- the ripening step is performed before proceeding to packaging,
- storage.

b) Studied strains:

Strain I-5305 as well as strain PC 12 (strain CHOOZIT PC12, Danisco) are tested with 2 final doses (D) of *Penicillium camemberti* for 100 kg retentate with ratios of PC12/I-5305 ranging from 0.5 to 1.5 D (1D=$2.10^9$ spores/mL).

Organoleptic Results:

The soft cheese with bloomy rind produced were submitted to a panel of experts throughout their life cycle Table 7 below shows the main characteristics of cheeses inoculated with 100% of strain PC 12 (strain CHOOZIT PC12, Danisco) and those having a combination of 50% strain of I-5305 associated with 50% of strain PC 12 (strain CHOOZIT PC12, Danisco).

At the semi-ripening stage of production (D+38 and D+45), there were significant differences between the 2 products with changes in appearance, rind texture and taste revealing a more advanced ripening stage on the cheese rind with the 100% strain PC 12 (strain CHOOZIT PC12, Danisco). The cheese with the addition of strain I-5305 allows the product to be stabilised in terms of colour and taste up to the product's use-by date, while maintaining a superior product quality throughout its shelf life.

EXAMPLE 6—USE OF A MIXTURE OF DIFFERENT STRAINS OF *P. CAMEMBERTI* FOR THE PRODUCTION OF GOAT'S CHEESE ACCORDING TO AN ULTRAFILTRATION METHOD, IN MIXED RIND

Materials and Methods:

a) Description of production steps:

The method of preparation of a goat's cheese according to an ultrafiltration method, in mixed rind comprises as the following main steps:
- preparing the pre-cheese which comprises the retentate, the cream, dairy proteins,
- heat treatment,
- incorporating lactic strains (*Lactococcus lactis* ssp *lactis, Lactococcus lactis* ssp *cremoris, Streptococcus thermophilus, Lactobacillus delbrueckii* ssp *bulgaricus*) and ripening ferments (*P. camemberti* and *Geotrichum candidum*) and rennet,
- dosage and acidification, up to a target pH of 5,
- cooling, demoulding and brining,
- ripening,
- drying,
- packaging,
- storage.

b) Studied strains:

Strain I-5305 as well as strain VELV-TOP®PC PR1 of Lallemand were tested at a dose of 4 doses/100 kg. They can be applied in combination with strains of *Geotrichum candidum* at 0.2 dose/100 kg (1 dose=$8.10^7$ UFC/ml).

Organoleptic Results:

The soft cheeses produced were submitted to a panel of experts for evaluation in the optimum age window at D+29.

TABLE 7

Main observations between the product made from strain PC 12 (strain CHOOZIT PC 12, Danisco) alone or in combination with strain I-5305 and monitoring of their evolution during ripening at D + 31, D + 38, D + 45, D + 59).

| Composition of the inoculation of the rind | D + 31 | D + 38 | D + 45 | D + 59 |
|---|---|---|---|---|
| 100% PC 12 | Rind slightly thick | White appearance, taste of rind "moisi-sylve-fungus" sandy rind texture | <u>Slightly yellow appearance</u> | <u>Yellow appearance, intensification of "moisi-sylvé" note grainy rind</u> |
| 50% I-5305 50% PC 12 | White appearance, below white rind | White appearance, below white rind | White appearance, below white rind | White appearance, below white rind |

*The date of inoculation is considered as D + 1
Underlined: appearance of ripening markers per product.

Table 8 below shows the main characteristics of cheeses according to the ripening strategy used.

TABLE 8

Comparison of cheeses inoculated with PC PR1 and I-5305 mixed with two ferments of *Geotrichum candidum* tasted by a panel of experts at D + 28.

|  | *Geotrichum candidum* and PC PR1 | *Geotrichum candidum* and I-5305 | *Geotrichum candidum* and PC PR1 | *Geotrichum candidum* and I-5305 |
|---|---|---|---|---|
| Appearance | Crinkled flower, yellow side and bottom & humid to touch | Crinkled flower, very white and not humid | Folded flower, yellow side and bottom & humid to touch | Folded flower, very white and not humid |
| Cut | Fine rind | Very fine rind | Fine rind | Very fine rind |
| Texture |  | Sticky but remains smooth Rind barely perceptible | Rind present, crisp | Sticky smooth Rind barely perceptible |
| Taste/smell | Intense cave type smell | Taste: softer, rounder, less aggressive Smell: less cave | Smell: very intense | Taste: softer, rounder, less aggressive Smell: more fungus |

In bold: the desired characteristics of the products.

It appears that all of the trials for mixed rind with the I-5305 strain show a qualitative gain in terms of colour, quality of the rind which is fine and barely perceptible and with a weaker smell.

The invention claimed is:

1. An isolated strain of *Penicillium camemberti* having a lag time on a milk culture medium at 4° C. longer than 19 days, said strain being strain I-5305, registered with the CNCM on 5 Apr. 2018.

2. A method for preparing a food product comprising a step of fermenting a food product with the *Penicillium camemberti* strain according to claim 1 thereby producing said food product.

3. The method according to claim 2, wherein the food product is a cheese, a vegetable matrix or a mixture of a vegetable matrix and a dairy material.

4. The method according to claim 2 wherein the fermentation step is performed with a mixture of surface strains comprising the *Penicillium camemberti* strain having a lag time on milk culture medium at 4° C. longer than 19 days, said strain being strain I-5305, registered with the CNCM on 5 Apr. 2018 and at least one other surface strain.

5. The method according to claim 4, wherein said other surface strain is *Geotrichum candidum*.

6. A fermented food product obtained by the method according to claim 2.

* * * * *